(12) United States Patent
Liu et al.

(10) Patent No.: US 12,281,252 B2
(45) Date of Patent: Apr. 22, 2025

(54) BIOLOGICAL WATER RETENTION MATERIAL, METHOD FOR PREPARING SAME AND USE THEREOF

(71) Applicants: SHANDONG ACADEMY OF FORESTRY, Shandong (CN); WEIFANG HUAWEI MATERIALS TECHNOLOGY CO., LTD., Shandong (CN)

(72) Inventors: Fangchun Liu, Jinan (CN); Honghai Han, Weifang (CN); Hailin Ma, Jinan (CN); Xiaokai Wang, Weifang (CN); Xiujuan Zhao, Jinan (CN); Lin Peng, Jinan (CN); Binghua Liu, Jinan (CN); Xinghong Liu, Jinan (CN)

(73) Assignees: SHANDONG ACADEMY OF FORESTRY, Shandong (CN); WEIFANG HUAWEI MATERIALS TECHNOLOGY CO., LTD., Shandong (CN)

( * ) Notice: Subject to any disclaimer, the term of this patent is extended or adjusted under 35 U.S.C. 154(b) by 0 days.

(21) Appl. No.: 18/032,246

(22) PCT Filed: Oct. 13, 2022

(86) PCT No.: PCT/CN2022/125151
§ 371 (c)(1),
(2) Date: Apr. 17, 2023

(87) PCT Pub. No.: WO2023/173735
PCT Pub. Date: Sep. 21, 2023

(65) Prior Publication Data
US 2024/0263075 A1 Aug. 8, 2024

(30) Foreign Application Priority Data

Mar. 17, 2022 (CN) .......................... 202210263233.5

(51) Int. Cl.
*C09K 17/48* (2006.01)
*A01N 63/22* (2020.01)
*C12N 1/20* (2006.01)
*C09K 101/00* (2006.01)

(52) U.S. Cl.
CPC .............. *C09K 17/48* (2013.01); *A01N 63/22* (2020.01); *C12N 1/20* (2013.01); *C09K 2101/00* (2013.01)

(58) Field of Classification Search
CPC ................................ A01N 63/22; A01N 25/10
See application file for complete search history.

(56) References Cited

U.S. PATENT DOCUMENTS

2024/0260570 A1* 8/2024 Bzducha ................ A01N 47/04

FOREIGN PATENT DOCUMENTS

| CN | 101792669 A | | 8/2010 | |
|---|---|---|---|---|
| CN | 103694052 A | | 4/2014 | |
| CN | 107011910 A | | 8/2017 | |
| CN | 109644818 A | * | 4/2019 | ............. A01G 24/15 |
| CN | 109679870 A | * | 4/2019 | ............. C05F 11/02 |
| CN | 111484950 A | | 8/2020 | |
| CN | 113951093 A | * | 1/2022 | ............. A01G 24/10 |
| CN | 114686398 A | | 7/2022 | |
| CN | 115777489 A | * | 3/2023 | |
| CN | 116553977 A | * | 8/2023 | ............. C05F 11/02 |
| RU | 2715380 C1 | | 2/2020 | |

OTHER PUBLICATIONS

Dec. 14, 2022 International Search Report issued in International Patent Application No. PCT/CN2022/125151.
Dec. 14, 2022 Written Opinion issued in International Patent Application No. PCT/CN2022/125151.

* cited by examiner

*Primary Examiner* — John Pak
(74) *Attorney, Agent, or Firm* — Oliff PLC

(57) ABSTRACT

A biological water retention material, a method for preparing the same and a use thereof. A *Bacillus subtilis*, named as *Bacillus subtilis* GE1, which has been deposited in China General Microbiological Culture Collection, Institute of Microbiology, Chinese Academy of Sciences on Jan. 7, 2016, with a deposit number of CGMCC No. 11964, solves the problem of lacking a biological water retention material that fully combines water retention materials with microbial agents to increase the survival rate of silviculture under drought conditions by increasing soil moisture content as well as enhancing the drought resistance of plants. It is suitable for use under drought and water shortage conditions, and can fully utilize the coupling effect of water retention and bacterial agents, increasing the survival rate of silviculture under drought conditions and promoting seedling growth by increasing soil moisture content as well as enhancing the drought resistance of plants.

20 Claims, 1 Drawing Sheet
Specification includes a Sequence Listing.

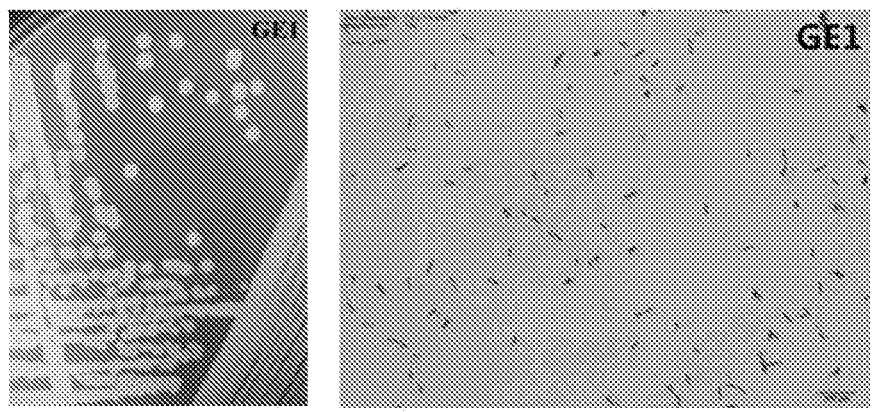

BIOLOGICAL WATER RETENTION MATERIAL, METHOD FOR PREPARING SAME AND USE THEREOF

CROSS-REFERENCE TO RELATED APPLICATIONS

The present disclosure claims priority to Chinese Application No. 202210263233.5 filed with the Chinese Patent Office on Mar. 17, 2022 and entitled "BIOLOGICAL WATER RETENTION MATERIAL, METHOD FOR PREPARING SAME AND USE THEREOF", the entire contents of which are incorporated herein by reference.

REFERENCE TO AN ELECTRONIC SEQUENCE LISTING

The present application contains a Sequence Listing that has been submitted electronically and is hereby incorporated by reference in its entirety. The electronic Sequence Listing is named 224079 Sequence Listing.xml, was created on Mar. 24, 2023, and is 3,610 bytes in size.

TECHNICAL FIELD

The present disclosure relates to the field of water retention materials, specifically to a biological water retention material, a method for preparing the same and a use thereof.

BACKGROUND

The information in this background is disclosed only to assist in understanding the general background according to the present disclosure and is not necessarily taken to acknowledge or otherwise suggest that the information constitutes prior art that is already well known to those of ordinary skill in the art.

It is well known that drought is a worldwide problem. The global arid and semi-arid areas account for about 35% of the land area. In China, arid and semi-arid areas are vast, involving 12 provinces, municipalities and autonomous regions in northeast, northwest and north China and covering about 52.5% of the total area of the country. These areas are rich in heat and light resources, have a large potential for agricultural production, and the water crisis in agriculture and forestry is showing a growing trend. Water scarcity is the primary factor limiting the economic development and ecological environment improvement in these areas.

The application of water retention and drought resistant materials to improve the soil's ability to store and retain water is an effective way to realize the greening of barren hills under the current water scarcity. A large number of studies have shown that soil water retention agent is a polymer with ultra-high water absorption and water retention capacity, which can enhance soil water retention, improve soil structure, reduce deep water seepage and soil nutrient loss, improve water utilization efficiency, and the like. In addition, the improvement of plant adaptation under drought conditions by inoculation of exogenous genes and artificial bacterial agents has become a hot research at home and abroad in recent years. The present inventors have screened *Bacillus cereus* L90 from rhizosphere soil of walnut suitable for application under drought conditions to improve the drought adaptation of walnut.

In view of the above, water retention materials can improve the plant adaptation under drought conditions by increasing soil moisture content, while inoculation of bacterial agents synthesize exogenously can induce stress resistance responses in plants, enhancing their own adaptive capacity in adversity. The prior art lacks a biological water retention material that fully combines water retention materials with microbial agents to increase the survival rate of silviculture under drought conditions by increasing soil moisture content as well as enhancing the drought resistance of plants.

SUMMARY

In order to solve the problems in the prior art, the present disclosure provides a biological water retention material, a method for preparing the same and a use thereof. According to the present disclosure, a biological water retention material is obtained by immobilizing functional microorganisms in the lattice of graft copolymer composite materials, which can enhance the plant adaptation and promote the plant growth under drought conditions in the case of both soil moisture contents and stress resistance responses in plants. A new technical solution is provided to fully utilize water resources and improve water use efficiency.

Specifically, the present disclosure is realized by the following technical solutions:

In a first aspect according to the present disclosure, there is provided a *Bacillus subtilis*, named as *Bacillus subtilis* GE1, which has been deposited in China General Microbiological Culture Collection, Institute of Microbiology, Chinese Academy of Sciences at NO.1 West Beichen Road, Chaoyang District, Beijing 100101, China on Jan. 7, 2016, with a deposit number of CGMCC No. 11964.

In a second aspect according to the present disclosure, there is provided a use of the above-mentioned *Bacillus subtilis* in improving plant stress resistance and promoting plant growth.

In a third aspect according to the present disclosure, there is provided a water retention material, the water retention material includes the above-mentioned *Bacillus subtilis* and a water retention agent.

In a fourth aspect according to the present disclosure, there is provided a method for preparing a water retention material, the method includes:
1) adding bentonite to water, adding potassium humate and a thiourea complexing agent to obtain the mixture;
2) adding a *Bacillus subtilis* GE1 powder mixture to the mixture to obtain a bacterial agent-bentonite-humic acid slurry for further use;
3) adding acrylic monomer into an agitator, stirring, slowly adding ammonia for neutralization, adjusting the pH of the solution to 6-8, adding acrylamide to obtain a neutralization solution at the end of the neutralization, and adding the adjusted neutralization solution into the bacterial agent-bentonite-humic acid slurry; and
4) adding a mixed cross-linking agent, adding APS or KPS as an initiator, then adding a redox initiation system consisting of $NaHSO_3$ or urea and stirring to obtain a viscous mixture, and continuing the reaction to generate a brown gel-like elastic graft copolymer composite material.

In a fifth aspect according to the present disclosure, there is provided a use of the water retention material and/or the method for preparing a water retention material as mentioned above in improving plant stress resistance and promoting plant growth.

One or more examples according to the present disclosure have the following beneficial effects:

1. The *Bacillus subtilis* GE1 according to the present disclosure has a stronger heat tolerance and salt tolerance and drought resistance, and can maintain a higher activity during the process of making biological water retention materials.
2. The process of making the water retention material according to the present disclosure can effectively immobilize *Bacillus subtilis* GE1 in the lattice of graft copolymer composite materials, while *Bacillus subtilis* GE1 can still maintain a higher activity, improving the biological effectiveness of GE1 under drought conditions.
3. The water retention material with biological activity according to the present disclosure not only has a strong function of water absorption and water retention, but also has certain biological activity with a number of effective viable bacteria of greater than $2.0 \times 10^7$ CFU/g.
4. The biological water retention material according to the present disclosure is suitable for use under drought and water shortage conditions, and can fully utilize the coupling effect of water retention and bacterial agents, increasing the survival rate of silviculture under drought conditions and promoting seedling growth by increasing soil moisture content as well as enhancing the drought resistance of plants.

BRIEF DESCRIPTION OF THE DRAWINGS

The accompanying drawings of the specification forming part of the present disclosure are used to provide a further understanding of the present disclosure, and the schematic examples according to the present disclosure and the descriptions thereof are used to explain the present disclosure and do not constitute an undue limitation of the present disclosure.

FIG. 1 is a graph showing the colony characteristics of *Bacillus subtilis* GE1 according to the present disclosure.

DETAILED DESCRIPTION

The present disclosure is further described below in conjunction with specific examples. It should be understood that these examples are only intended to illustrate the present disclosure and are not intended to limit the scope of the present disclosure. Experimental methods for which specific conditions are not indicated in the following examples, and usually follow conventional conditions or follow the conditions recommended by the manufacturer.

Unless otherwise defined, all professional and scientific terms as used herein have the same meaning as those familiar to those skilled in the art. In addition, any method and material similar or equivalent to what is described can be applied to the method according to the present disclosure. The preferred methods and materials described herein are for illustration purposes only. The mixed cross-linking agent used in the present disclosure can be a combination of any two or more cross-linking agents, as long as the cross-linking effect can be achieved. Specifically, the mixed cross-linking agent can be a combination of N, N'-methylenebisacrylamide and polyvinyl alcohol.

The prior art lacks a biological water retention material that fully combines water retention materials with microbial agents to increase the survival rate of silviculture under drought conditions by increasing soil moisture content as well as enhancing the drought resistance of plants. The purpose of the present disclosure is to provide a biological water retention material and a method for preparing the same. The material contains a plant growth promoting rhizobacteria with drought-resistant and growth-promoting functions and has a stronger water retention function, and thus can fully play the dual role of water retention and functional microorganism.

In a first aspect according to the present disclosure, there is provided a *Bacillus subtilis*, named as *Bacillus subtilis* GE1, which has been deposited in China General Microbiological Culture Collection, Institute of Microbiology, Chinese Academy of Sciences on Jan. 7, 2016, with a deposit number of CGMCC No. 11964.

In a second aspect according to the present disclosure, there is provided a use of the above-mentioned *Bacillus subtilis* in improving plant stress resistance and promoting plant growth.

Preferably, the stress resistance includes heat tolerance, salt tolerance and drought resistance.

Preferably, the plant is a seedling; further preferably, the plant is an elderberry.

In a third aspect according to the present disclosure, there is provided a water retention material, the water retention material includes the above-mentioned *Bacillus subtilis* and a water retention agent.

Preferably, the water retention agent is a graft copolymer composite material.

Preferably, the *Bacillus subtilis* GE1 is immobilized in the lattice of graft copolymer composite materials.

In some examples, the raw materials for the water retention agent include bentonite, potassium humate, acrylic acid, acrylamide, and redox initiation system.

Preferably, the redox initiation system is selected from APS (ammonium persulfate) and/or KPS (potassium persulfate), $NaHSO_3$ and/or urea.

In some examples, the water retention material includes a *Bacillus subtilis* GE1 powder mixture. The *Bacillus subtilis* GE1 powder mixture is made by mixing a concentrated preparation of *Bacillus subtilis* GE1 and glycerol.

Preferably, the *Bacillus subtilis* GE1 powder mixture is made by mixing a microbial concentrated preparation of *Bacillus subtilis* GE1 and glycerol at the ratio of 1:(2-3).

Preferably, in the water retention material, *Bacillus subtilis* GE1 powder mixture:bentonite:potassium humate:acrylic acid:acrylamide is (1-3):(30-40):(1-5):(50-60):(0-20).

In a fourth aspect according to the present disclosure, there is provided a method for preparing a water retention material, the method includes:
1) bentonite is added to water, potassium humate and a thiourea complexing agent are added to obtain the mixture;
2) a *Bacillus subtilis* GE1 powder mixture is added to the mixture to obtain a bacterial agent-bentonite-humic acid slurry for further use;
3) acrylic monomer is added into an agitator, stirred, ammonia is slowly added for neutralization, the pH of the solution is added to 6-8, acrylamide is added to obtain a neutralization solution at the end of the neutralization, and the adjusted neutralization solution is added into the bacterial agent-bentonite-humic acid slurry; and
4) a mixed cross-linking agent is added, APS or KPS is added as an initiator, then a redox initiation system consisting of $NaHSO_3$ or urea is added and stirred to obtain a viscous mixture, and the reaction is continued to generate a brown gel-like elastic graft copolymer composite material.

In some examples, in step 1), bentonite is added to an appropriate amount of water, stirred for 30-40 min, potassium humate is added, stirred for 20-30 min, then a thiourea complexing agent is added and stirred for 15-30 min to obtain the mixture.

In some examples, in step 3), the temperature is maintained at no more than 60° C. when the ammonia solution is added for neutralization.

In some examples, in step 4), a mixed cross-linking agent is added, the temperature is controlled at 20-40° C., stirred for 15-30 min, APS or KPS as an initiator is added, stirred for 3-7 min, a redox initiation system consisting of NaHSO$_3$ or urea is added, stirred for 1-3 min to obtain a viscous mixture, and a brown gel-like elastic graft copolymer composite material is generated.

Preferably, APS or KPS as the initiator is added and stirred for 5 min.

Preferably, the redox initiation system is added and stirred for 2 min.

Preferably, after obtaining a viscous mixture, the reaction is continued in an oven at 55-65° C. to generate a brown gel-like elastic graft copolymer composite material; further preferably, the reaction is continued in an oven at 60° C.

In a fifth aspect according to the present disclosure, there is provided a use of the water retention material and/or the method for preparing a water retention material as mentioned above in improving plant stress resistance and promoting plant growth.

Preferably, the stress resistance includes heat tolerance, salt tolerance and drought resistance.

In some examples, the method for preparing the water retention material is as follows:
1. The bentonite is added to the appropriate amount of water, stirred for 30-40 min, potassium humate is added in turn, stirred for 20-30 min and then a thiourea is added complexing agent, stirred for 15-30 min to obtain the mixture.

The number of added parts of bentonite is 30-40.

The number of added parts of potassium humate is 1-5.

2. The bacterial powder mixture is added to the mixture, the strain and the mixture are evenly mixed upon stirring for 10 min to obtain a bacterial agent-bentonite-humic acid slurry for further use.

The bacterial powder mixture is made by evenly mixing a microbial concentrated preparation and glycerol at the ratio of 1:(2-3).

The microbial concentrated preparation is made by spray drying *Bacillus subtilis* GE1.

The *Bacillus subtilis* GE1 has been deposited in China General Microbiological Culture Collection, Institute of Microbiology, Chinese Academy of Sciences on Jan. 7, 2016, with a deposit number of CGMCC No. 11964.

The colonies of *Bacillus subtilis* GE1 are characterized by: the colonies of GE1 strain in LB medium being round and irregular with a colony size of about 5 mm after culturing for 24 h, having a dry and lusterless surface, an untidy edge, a brownish-yellow color with a darker color in the middle, being opaque and having spores.

The number of added parts of bacterial powder mixture is 1-3.

3) Acrylic monomer is added into an agitator, stirred, an ammonia solution is slowly added for neutralization, the temperature is maintained at no more than 60° C. and the pH of the solution is adjusted to 6-8. The acrylamide is added after the neutralization is completed.

The adjusted neutralization solution is then added to the bacterial agent-bentonite-humic acid stock slurry and mixed well upon stirring.

The number of added parts of acrylic acid is 50-60.

The number of added parts of acrylamide is 0-20.

4. A mixed cross-linking agent is added, the temperature is controlled at 20-40° C., and stirred for 15-30 min; APS or KPS are added as an initiator and stirred for 5 min; a redox initiation system consisting of NaHSO$_3$ or urea is added and stirred for 2 min to obtain a viscous mixture; the reaction is continued in an oven at 60° C. to generate a brown gel-like elastic graft copolymer composite material. This material has a cross-linked molecular structure, is biologically active and has a good water retention property.

Example 1: Identification of *Bacillus subtilis* GE1

The *Bacillus subtilis* GE1 according to the present disclosure was obtained from screening by this applicant.

As shown in FIG. 1, the colonies of plant growth promoting rhizobacteria according to the present disclosure are characterized by: the colonies of GE1 strain in LB medium being round and irregular with a colony size of about 3 mm after culturing for 24 h, having a dry and lusterless surface, a tidy edge, being white and opaque and having spores.

The specific 16S rDNA sequence of *Bacillus subtilis* GE1 is shown in sequence SEQ ID NO: 1 as follows:

```
tgcagtcgagcggacagatgggagcttgctccctgatgttagcggcgga cgggtgagtaacacgtgggtaacctgcctgtaagactgggataactccg ggaaaccggggctaataccggatggttgtttgaaccgcatggttcaaac ataaaaggtggcttcggctaccacttacagatggacccgcggcgcatta gctagttggtgaggtaacggctcaccaaggcaacgatgcgtagccgacc tgagagggtgatcggccacactgggactgagacacggcccagactccta cgggaggcagcagtagggaatcttccgcaatggacgaaagtctgacgga gcaacgccgcgtgagtgatgaaggttttcggatcgtaaagctctgttgt tagggaagaacaagtaccgttcgaatagggcggtaccttgacggtacct aaccagaaagccacggctaactacgtgccagcagccgcggtaatacgta ggtggcaagcgttgtccggaattattgggcgtaaagggctcgcaggcgg tttcttaagtctgatgtgaaagccccggctcaaccggggagggtcatt ggaaactggggaacttgagtgcagaagaggagagtggaattccacgtgt agcggtgaaatgcgtagagatgtggaggaacaccagtggcgaaggcgac tctctggtctgtaactgacgctgaggagcgaaagcgtggggagcgaaca ggattagataccctggtagtccacgccgtaaacgatgagtgctaagtgt taggggtttccgcccttagtgctgcagctaacgcattaagcactccg cctggggagtacggtcgcaagactgaaactcaaaggaattgacgggggc ccgcacaagcggtggagcatgtggtttaattcgaagcaacgcgaagaac cttaccaggtcttgacatcctctgacaatcctagagataggacgtcccc ttcgggggcagagtgacaggtggtgcatggttgtcgtcagctcgtgtcg tgagatgttgggttaagtcccgcaacgagcgcaacccttgatcttagtt gccagcattcagttgggcactctaaggtgactgccggtgacaaaccgga
```

-continued

```
ggaaggtggggatgacgtcaaatcatcatgcccttatgacctgggcta cacacgtgctacaatggacagaacaaagggcagcgaaaccgcgaggtta agccaatcccacaaatctgttctcagttcggatcgcagtctgcaactcg actgcgtgaagctggaatcgctagtaatcgcggatcagcatgccgcggt gaatacgttcccgggccttgtacacaccgcccgtcacaccacgagagtt tgtaacacccgaagtcggtgaggtaaccttttaggagccagccgccgaa
```

The physiological and biochemical characteristics of *Bacillus subtilis* GE1 are shown in Table 1 below.

TABLE 1

Physiological and biochemical characteristics of GE1 strain

| Characteristics | *Bacillus subtilis* | GE1 |
|---|---|---|
| Cell diameter >1 μm | − | − |
| Round spores | − | − |
| Exposure to enzymes | + | + |
| Anaerobic growth | − | − |
| V-P determination | + | + |
| Acid production: D-glucose | + | + |
| Gas production from glucose | − | − |
| Amylohydrolysis | + | + |
| Utilization: Citrate | + | + |
| Propionate | − | − |
| Tyrosine hydrolysis | − | − |
| Phenylalanine deaminase | − | − |
| Yolk lecithinase | − | − |
| Indole formation | − | − |

The 16S rRNA gene sequence of GE1 was compared with that in the Genbank database by BLAST analysis. The results show that GE1 is in the same branch with *Bacillus subtillis* and *Bacillus licheniformis* in the phylogenetic tree with a similarity of 100%. The GE1 is identified as *Bacillus subtilis* by combining physiological and biochemical characteristics and morphological characteristics of the colonies.

The measurement results of the protease production by the *Bacillus subtilis* GE1 are shown in Table 2 below.

TABLE 2

Protease activity assay of GE1 strain

| Strain No. | Transparent zone diameter D (mm) | Colony diameter d (mm) | D/d | Protease activity in fermentation broth (μg/ml) |
|---|---|---|---|---|
| GE1 | 22.15 | 8.01 | 2.77 | 48.26 |

Example 2: Activity of Different Bacterial Agents in the Production of Water Retention Materials According to the same spray drying process, *Bacillus subtilis* GE1, *Bacillus subtilis* GE3, and *Bacillus subtilis* DZ1 were formulated into microbial concentrated preparations respectively. Six treatments were designed when making different bacterial powder mixtures: 1) a GE1 concentrated preparation was mixed with glycerol at a ratio of 1:2; 2) a GE3 concentrated preparation was mixed with glycerol at a ratio of 1:2; 3) a DZ1 concentrated preparation was mixed with glycerol at a ratio of 1:2; 4) a GE1 concentrated preparation was directly used for obtaining water retention materials without adding glycerol; 5) a GE3 concentrated preparation was directly used for obtaining water retention materials without adding glycerol; and 6) DZ1 concentrated preparation was directed used for obtaining water retention materials without adding glycerol. Subsequently, water retention materials were produced according to the corresponding production process. Microbial count results for the final materials (number of effective viable bacteria for each material) are shown in the table below.

TABLE 3

Microbial count of the materials in different treatments

| Treatment | Microorganisms (CFU/g) |
|---|---|
| *Bacillus subtilis* GE1 + glycerol | $3.2 \times 10^7$ a |
| *Bacillus subtilis* GE3 + glycerol | $2.6 \times 10^4$ c |
| *Bacillus subtilis* DZ1 + glycerol | $9.3 \times 10^4$ c |
| *Bacillus subtilis* GE1 | $5.2 \times 10^5$ b |
| *Bacillus subtilis* GE3 | $1.2 \times 10^2$ d |
| *Bacillus subtilis* DZ1 | $8.3 \times 10^2$ d |

It can be seen that for *Bacillus subtilis* GE1 according to this application, the final material can achieve a microbial count of $3.2 \times 10^7$ CFU/g, while only $2.6 \times 10^4$ and $9.3 \times 10^4$ can be achieved for GE3 and DZ1, respectively. In addition, the addition of glycerol to the bacterial powder mixture greatly increases the microbial activity. It can be seen that the *Bacillus subtilis* GE1 according to this application, which has the least reduction in effectiveness in the production process of water retention materials, is better adapted to the production process of water retention materials. Also, the addition of glycerol during the production process is a technical means to effectively increase microbial activity.

Example 3: Test for Drought Resistant in Plants

The water retention material with biological activity were prepared by 2 parts of the bacterial powder mixture.

A pot experiment was used, in which the plastic pots were 28 cm in height, 30 cm in top diameter and 19 cm in bottom diameter. The nursery soil was mixed with sand at a volume ratio of 3:1 as the base soil, and each pot was filled with 10 kg of soil. Four test treatments were set up: 1) *Bacillus subtilis* GE1; 2) a water retention material made without GE1; 3) a mixture of *Bacillus subtilis* GE1 and a water retention material made without GE1; and 4) a water retention material with biological activity according to the present disclosure.

The elderberry seedlings with consistent growth were selected and transplanted in pots, one per pot, and tested in the greenhouse of the experimental nursery at Shandong Forestry Research Institute. The amount of water retention materials accounted for 0.2% of soil weight (20 g) and the amount of *Bacillus subtilis* GE1 powder mixture was 0.4 g. The different test materials were mixed with soil according to the treatments, and the elderberry seedlings with consistent growth were selected and transplanted into pots, one per pot, and tested in the greenhouse of the experimental nursery at Shandong Forestry Research Institute. After 60 d of normal management, drought stress was initiated while controlling the moisture content to about 40% of the field water-holding capacity. After 23 d, leaf photosynthetic rate, relative moisture content, chlorophyll content, and aboveground dry weight were measured. The results show that the water retention materials with biological activity according to the present disclosure can improve the leaf photosynthetic rate, increase the relative moisture content and chlorophyll content of the leaves, and also enhance the dry matter accumulation in the aboveground part, compared with other treatments. Therefore, the water retention materials with biological activity according to the present disclosure can improve the drought resistance of seedlings under drought conditions.

TABLE 4

Physiological characteristics of plants in different treatments

| No. | Photosynthetic rate/ $\mu mol/(m \cdot s)$ | Relative moisture content/% | Chlorophyll/ $mg \cdot g^{-1}$ | Aboveground dry weight/g |
|---|---|---|---|---|
| 1 | 7.99 b | 63.46 b | 2.12 b | 21.16 b |
| 2 | 7.64 b | 61.34 b | 1.94 c | 22.86 b |
| 3 | 7.92 b | 62.91 b | 1.87 c | 22.98 b |
| 4 | 9.81 a | 68.21 a | 2.37 a | 26.23 a |

The above contents as disclosed are only preferred examples according to the present disclosure, which of course cannot be used to limit the scope of the present disclosure. Therefore, the equivalent changes made within the scope of the patent application are still covered by the present disclosure.

of the neutralization, and adding the pH-adjusted neutralization solution into the bacterial agent-bentonite-humic acid slurry; and 4) adding a mixed cross-linking agent, adding ammonium persulfate or potassium persulfate as an initiator, then adding a redox initiation system consisting of $NaHSO_3$ or urea and stirring to obtain a viscous mixture, and continuing the reaction to generate the water retention material, wherein:

the water retention material is a brown gel-like elastic graft copolymer composite material; and the *Bacillus subtilis* GE1 has been deposited in China General Microbiological Culture Collection, Institute of Microbiology, Chinese Academy of Sciences on Jan. 7, 2016, with a deposit number of CGMCC No. 11964.

2. The method for preparing a water retention material according to claim 1, wherein the *Bacillus subtilis* GE1 powder mixture is made by mixing a concentrated preparation of *Bacillus subtilis* GE1 and glycerol.

3. The method for preparing a water retention material according to claim 2, wherein said *Bacillus subtilis* GE1

What is claimed is:

1. A method for preparing a water retention material, the method comprising:

1) adding bentonite, potassium humate, and thiourea to water to obtain a mixture;

2) adding a *Bacillus subtilis* GE1 powder mixture to the mixture to obtain a bacterial agent-bentonite-humic acid slurry for further use;

3) adding acrylic monomer into an agitator, stirring, slowly adding ammonia for neutralization to obtain a solution, adjusting the pH of the solution to 6-8, adding acrylamide to obtain a neutralization solution at the end powder mixture is made by mixing a concentrated preparation of *Bacillus subtilis* GE1 and glycerol at the ratio of 1:(2-3).

4. The method for preparing a water retention material according to claim 1, wherein, in step 1), the bentonite is added to the water, stirred for 30-40 min, the potassium humate is added, stirred for 20-30 min, and then the thiourea is added and stirred for 15-30 min to obtain the mixture.

5. The method for preparing a water retention material according to claim 1, wherein, in step 3), the temperature is maintained at no more than 60° C. when an ammonia solution is added for neutralization.

6. The method for preparing a water retention material according to claim 1, wherein, in step 4), the mixed cross-linking agent is added, the temperature is controlled at 20-40° C., stirred for 15-30 min, the ammonium persulfate or potassium persulfate as an initiator is added, stirred for 3-7 min, the redox initiation system consisting of $NaHSO_3$ or urea is added, stirred for 1-3 min to obtain the viscous mixture, and the water retention material is generated.

7. The method for preparing a water retention material according to claim 6, wherein the ammonium persulfate or potassium persulfate as the initiator is added and stirred for 5 min.

8. The method for preparing a water retention material according to claim 6, wherein the redox initiation system is added and stirred for 2 min.

9. The method for preparing a water retention material according to claim 6, wherein, after obtaining the viscous mixture, the reaction is continued in an oven at 55-65° C. to generate the water retention material.

10. The method for preparing a water retention material according to claim 9, wherein the reaction is continued in an oven at 60° C.

11. A method comprising:
preparing a water retention material according to claim 1;
mixing the water retention material in soil to improve plant stress resistance, the stress resistance being drought resistance, and to promote plant growth; and
planting or transplanting at least one plant into the soil mixed with the water retention material.

12. A method comprising:
preparing a water retention material according to claim 2;
mixing the water retention material in soil to improve plant stress resistance, the stress resistance being drought resistance, and to promote plant growth; and
planting or transplanting at least one plant into the soil mixed with the water retention material.

13. A method comprising:
preparing a water retention material according to claim 3;
mixing the water retention material in soil to improve plant stress resistance, the stress resistance being drought resistance, and to promote plant growth; and
planting or transplanting at least one plant into the soil mixed with the water retention material.

14. A method comprising:
preparing a water retention material according to claim 4;
mixing the water retention material in soil to improve plant stress resistance, the stress resistance being drought resistance, and to promote plant growth; and
planting or transplanting at least one plant into the soil mixed with the water retention material.

15. A method comprising:
preparing a water retention material according to claim 5;
mixing the water retention material in soil to improve plant stress resistance, the stress resistance being drought resistance, and to promote plant growth; and
planting or transplanting at least one plant into the soil mixed with the water retention material.

16. A method comprising:
preparing a water retention material according to claim 6;
mixing the water retention material in soil to improve plant stress resistance, the stress resistance being drought resistance, and to promote plant growth; and
planting or transplanting at least one plant into the soil mixed with the water retention material.

17. A method comprising:
preparing a water retention material according to claim 7;
mixing the water retention material in soil to improve plant stress resistance, the stress resistance being drought resistance, and to promote plant growth; and
planting or transplanting at least one plant into the soil mixed with the water retention material.

18. A method comprising:
preparing a water retention material according to claim 8;
mixing the water retention material in soil to improve plant stress resistance, the stress resistance being drought resistance, and to promote plant growth; and
planting or transplanting at least one plant into the soil mixed with the water retention material.

19. A method comprising:
preparing a water retention material according to claim 9;
mixing the water retention material in soil to improve plant stress resistance, the stress resistance being drought resistance, and to promote plant growth; and
planting or transplanting at least one plant into the soil mixed with the water retention material.

20. A method comprising:
preparing a water retention material according to claim 10;
mixing the water retention material in soil to improve plant stress resistance, the stress resistance being drought resistance, and to promote plant growth; and
planting or transplanting at least one plant into the soil mixed with the water retention material.

* * * * *

SEQUENCE LISTING

```
Sequence total quantity: 1
SEQ ID NO: 1              moltype = DNA  length = 1421
FEATURE                   Location/Qualifiers
source                    1..1421
                          mol_type = genomic DNA
                          organism = Bacillus subtilis
                          strain = GE1
SEQUENCE: 1
tgcagtcgag cggacagatg ggagcttgct ccctgatgtt agcggcggac gggtgagtaa   60
cacgtgggta acctgcctgt aagactggga taactccggg aaaccggggc taataccgga  120
tggttgtttg aaccgcatgg ttcaaacata aaaggtggct tcggctacca cttacagatg  180
gacccgcggc gcattagcta gttggtgagg taacggctca ccaaggcaac gatgcgtagc  240
cgacctgaga gggtgatcgg ccacactggg actgagacac ggcccagact cctacgggag  300
gcagcagtag ggaatcttcc gcaatggacg aaagtctgac ggagcaacgc cgcgtgagtg  360
atgaaggttt tcggatcgta aagctctgtt gttagggaag aacaagtacc gttcgaatag  420
ggcggtacct tgacggtacc taaccagaaa gccacggcta actacgtgcc agcagccgcg  480
gtaatacgta ggtggcaagc gttgtccgga attattgggc gtaaagggct cgcaggcggt  540
ttcttaagtc tgatgtgaaa gccccccggct caaccgggga gggtcattgg aaactgggga  600
acttgagtgc agaagaggag agtggaattc cacgtgtagc ggtgaaatgc gtagagatgt  660
ggaggaacac cagtggcgaa ggcgactctc tggtctgtaa ctgacgctga ggagcgaaag  720
cgtggggagc gaacaggatt agataccctg gtagtccacg ccgtaaacga tgagtgctaa  780
gtgttagggg gtttccgccc cttagtgctg cagctaacgc attaagcact ccgcctgggg  840
agtacggtcg caagactgaa actcaaagga attgacgggg gcccgcacaa gcggtggagc  900
atgtggttta attcgaagca acgcgaagaa ccttaccagg tcttgacatc ctctgacaat  960
cctagagata ggacgtcccc ttcgggggca gagtgacagg tggtgcatgg ttgtcgtcag 1020
ctcgtgtcgt gagatgttgg gttaagtccc gcaacgagcg caaccctgga tcttagttgc 1080
cagcattcag ttgggcactc taaggtgact gccggtgaca aaccggagga aggtggggat 1140
gacgtcaaat catcatgccc cttatgacct gggctacaca cgtgctacaa tggacagaac 1200
aaagggcagc gaaaccgcga ggttaagcca atcccacaaa tctgttctca gttcggatcg 1260
cagtctgcaa ctcgactgcg tgaagctgga atcgctagta atcgcggatc agcatgccgc 1320
ggtgaatacg ttcccgggcc ttgtacacac cgcccgtcac accacgagag tttgtaacac 1380
ccgaagtcgg tgaggtaacc ttttaggagc cagccgccga a                    1421
```